(12) United States Patent
Harenberg et al.

(10) Patent No.: US 9,944,971 B2
(45) Date of Patent: Apr. 17, 2018

(54) DETERMINATION OF DIRECT THROMBIN INHIBITORS IN FLUIDS LIKE SERUM OR URINE

(75) Inventors: Job Harenberg, Heidelberg (DE); Roland Kramer, Munster (DE)

(73) Assignee: DOASENSE GmbH (DE)

( * ) Notice: Subject to any disclaimer, the term of this patent is extended or adjusted under 35 U.S.C. 154(b) by 287 days.

(21) Appl. No.: 14/128,402

(22) PCT Filed: Jun. 15, 2012

(86) PCT No.: PCT/EP2012/002540
§ 371 (c)(1),
(2), (4) Date: Mar. 20, 2014

(87) PCT Pub. No.: WO2012/175183
PCT Pub. Date: Dec. 27, 2012

(65) Prior Publication Data
US 2014/0220611 A1   Aug. 7, 2014

(30) Foreign Application Priority Data
Jun. 22, 2011  (GB) .................................. 111502.0

(51) Int. Cl.
*C12Q 1/37* (2006.01)
*C12Q 1/56* (2006.01)

(52) U.S. Cl.
CPC  *C12Q 1/37* (2013.01); *C12Q 1/56* (2013.01)

(58) Field of Classification Search
None
See application file for complete search history.

(56) References Cited

U.S. PATENT DOCUMENTS

| | | | | |
|---|---|---|---|---|
| 4,252,715 A | * | 2/1981 | Aurell ................... | C07K 5/0819 435/23 |
| 5,320,945 A | * | 6/1994 | Dessauer ................ | C12Q 1/56 435/13 |

FOREIGN PATENT DOCUMENTS

WO   WO 1993/022453 A1   11/1993

OTHER PUBLICATIONS

Grießbach et al. "Assay of hirudin in plasma using a chromogenic thrombin substrate." Thrombosis research 37(2): 347-350, 1985.*
Gallwitz et al. "The extended cleavage specificity of human thrombin", PloS One 7(2): e31756, 2012.*
Kastrup et al. "Characterization of the threshold response of initiation of blood clotting to stimulus patch size", Biophysical Journal 93(8): 2969-2977, 2007.*
Griebetabach et al., "Assay of hirudin in plasma using a chromogenic thrombin substrate", XP022879763, *Thrombosis Research*, vol. 37 (2), 347-350 (1985).
Harenberg et al., "Measurement of Dabigatran in Serum and Urine and as Point of Care Method in Urine", XP002686276, Database Accession No. PREV201200220631 Database Biosis [Online] Biosciences Information Service, Blood vol. 118, 1438 (21) 2011.
Hoffmann et al., "Comparison of three methods for measuring PEG-hirudin in blood", *Blood Coagulation & Fibrinolysis*, vol. 12(7), 577-581 (2001).
Lange et al., "Ecarin chromogenic assay—A new method for quantitative determination of direct thrombin inhibitors like hirudin", *Pathophysiology of Haemostasis and Thrombosis*, vol. 33 (4), 184-191 (2003).
Nowak et al.. "Pharmacology of r-hirudin in renal impairment", *Thrombosis Research*, vol. 66 (6), 707-715 (1992).
Patent Cooperation Treaty, International Searching Authority, Search Report and Written Opinion for PCT/EP2012/002540, 12 pages, Nov. 26, 2012.
Stangier et al., "The pharmacokinetics, pharmacodynamics and tolerability of dabigatran etexilate, a new oral direct thrombin inhibitor, in healthy male subjects", British Journal of Clinical Pharmacology, vol. 64 (3). 292-303 (2007).
Bucha, et al., "In vitro study of r-hirudin permeability through membranes of different haemodialysers", Nephrol Dial Transplant 14, 2922-2926 (1999).
Chiu, et al., "Matrix Effects—A Challenge Toward Automation of Molecular Analysis", JALA 233-242 (Jun. 2010).
Gray, et al., "Collaborative study onmonitoring mehtods to determine direct thrombin inhibitors lepirudin and argatroban", Journal of Thrombosis and Haemostasis 3, 2096-2097 (2005).
Grutter, et al., "Crystal structure of the thrombin-hirudin complex: a novel mode of serine protease inhibition", The EMBO Journal vol. 9 (8), 2361-2365 (1990).
Hankey, et al., "Dabigatran Etexilate—A New Oral Thrombin Inhibitor", Circulation 123, 1436-1450 (2011).
Hiebert, et al., "Increased plasma anti-Xa activity and recovery of heparin from urine suggest absorption of orally administered unfractionated heparin in human subjects", J Lab Clin Med 145, 151-155 (2005).
O'Brien, et al., "Direct Thrombin Inhibitors", Journal of Cardiovascular Pharmacology and Therapeutics 17 (1), 5-11 (2012).
Zavyalova, et al., "Multiple inhibitory kinetics reveal an allosteric interplay among thrombin functional sites", Thrombosis Research 135, 212-216 (2015).

* cited by examiner

*Primary Examiner* — Emily A Cordas
(74) *Attorney, Agent, or Firm* — Viksnins Harris Padys Malen LLP

(57) ABSTRACT

The present invention relates to a method for detecting at least one direct thrombin inhibitor in a sample other than citrate plasma, comprising the step of mixing a sample containing a thrombin inhibitor with a composition containing thrombin under conditions which allow the thrombin to release a detectable substance from a chromogenic substrate.

8 Claims, 3 Drawing Sheets

DETERMINATION OF DIRECT THROMBIN INHIBITORS IN FLUIDS LIKE SERUM OR URINE

CROSS-REFERENCE TO RELATED APPLICATION(S)

Figure 1:
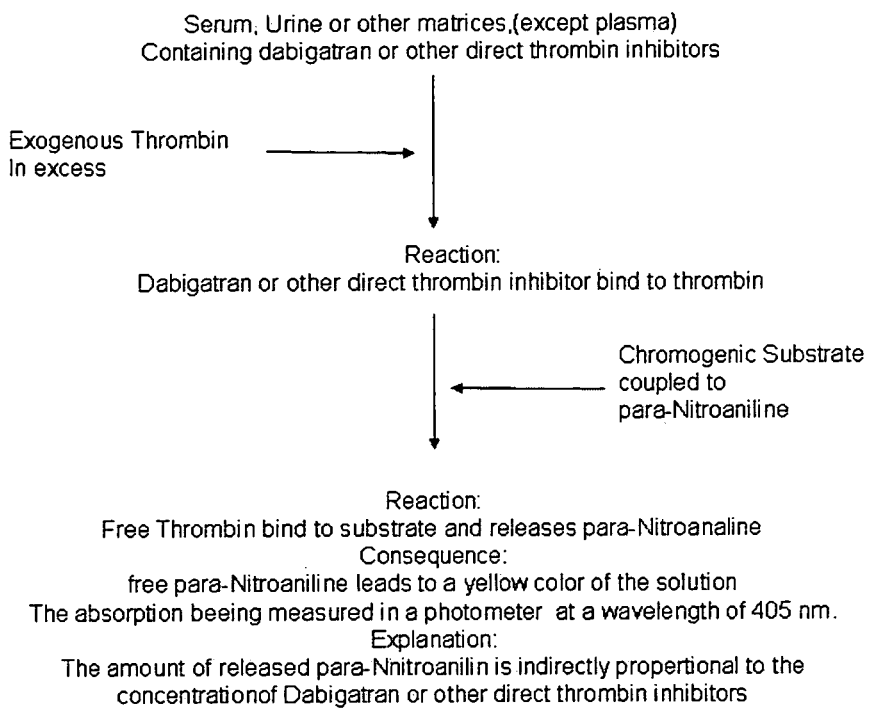

This patent application claims the benefit of priority of United Kingdom Application Serial No. GB111502.0, filed on Jun. 22, 2011.

DESCRIPTION

The present invention relates to a method for detecting at least one direct thrombin inhibitor in a sample other than citrate plasma, comprising the step of mixing a sample containing a thrombin inhibitor with a composition containing thrombin under conditions which allow the thrombin to release a detectable substance from a substrate.

Coagulation tests of blood are conducted on plasma samples from humans/animals by making blood samples incoagulable with sodium citrate (volume ratio blood/anticoagulant 9:1). To conduct the determination of individual measurement values of the blood coagulation, blood is centrifuged and the cells (in the sediment) are separated from the liquid blood components (plasma). To measure the coagulation time of plasma, calcium chloride and an activator of the coagulation are added to the plasma. In special methods for determining individual clotting factors or exogenous inhibitors, photometric proof is used. In these methods, the colorant para-nitroaniline is released by an exogenously added coagulation enzyme (e.g. thrombin) from a chromogenic substrate (Benzyl-Isoleucine-Glutamine-Glycine-Arginine-para-nitroaniline hydrochloride, Tosyl-Glycine-Proline-Arginine-para-nitroaniline, rhodamine 110, bis-p-tosyl-L-glycyl-L-prolyl-L-arginine amide (Zweig S E et al, Membrane based, dry-reagent prothrombin time test, Biomed Instrum Technol (1996) 30:245-256) and others), the activity/concentration of thrombin inhibitors or substances inhibiting thrombin being measured in a concentration-dependent manner. The result is a linear or sigmoidal decrease of the release of para-nitroaniline, measured at 405 nanometers in the photometer, depending on the concentration of the thrombin inhibitor (Gray E, Harenberg J. Collaborative study on monitoring methods to determine direct thrombin inhibitors lepirudin and argatroban. ISTH Control of Anticoagulation SSC Working Group on Thrombin Inhibitor. Journal of Thrombosis and Haemostasis. 2005 September; 3(9):2096-7).

If one aims to analyze other parameters than for blood coagulation, such as kidney or liver function parameters, electrolytes or cholesterol, blood is coagulated by the addition of an activator (e.g. kaolin). Here, the coagulation proteins, antithrombin and fibrinogen are used. These factors are mixed with blood cells in a blood clot in the coagulum in a coagulation tube, into which blood is withdrawn. Serum can be found in the supernatant, which does not contain these coagulation proteins. The measurement of these clinical-chemical parameters is easier in serum. Concentrations of drugs are measured in serum as well, except for the coagulation drugs for clinical use.

Heparins, low-molecular-weight heparins, heparinoids, fondaparinux and other polysaccharides need cofactors in the blood (antithrombin, heparin cofactor II) to activate their anticoagulative effect towards coagulation enzymes such as thrombin. These cofactors are present in plasma, so that citrate plasma samples are used for analyzing the activity of the inhibitors of blood coagulation. Tests in serum are not possible with methods for the clinical routine (Harenberg J, Neue Antikoagulantien. Zett Verlag, Steinen, 2007).

Direct thrombin inhibitors do not need cofactors in the blood to become active. These are so-called direct coagulation inhibitors of coagulation enzymes. The most important ones for the time being are the group of direct thrombin and thrombin inhibitors. Their activity/concentration is measured in citrate plasma with different methods/activators. Dabigatran is the second of the oral direct thrombin inhibitors to be clinically used. Ximelagatran, the first oral direct thrombin inhibitor, has been withdrawn from the market due to several intolerances in patients. The relevant determination methods for detecting the concentration/activity of dabigatran are published. All analyses are made with plasma anticoagulated with citrate (Stangier J, et al. The pharmacokinetics, pharmacodynamics and tolerability of dabigatran etexilate, a new oral direct thrombin inhibitor, in healthy male subjects. Br J Clin Pharmacol. 2007; 64:292-303).

The determination of the concentration of dabigatran adopts high pressure liquid chromatography, a method, which cannot be adopted for clinical routine.

So far, there have not been any detection methods in the clinical-chemical routine for inhibitors of blood coagulation from serum. Serum has different advantages over plasma: In medicine, serum samples are more often taken from patients than plasma samples. The blood withdrawal is less susceptible to influences for serum samples than for plasma samples. In the case of a "bad" blood withdrawal, blood coagulation can be activated. Thereby, the results are influenced by the clotting factors. This is not possible for serum samples, since a blood coagulation is performed in the tube after the withdrawal.

Current solutions have the disadvantage of requiring a separate blood withdrawal for obtaining plasma samples for the analysis. Thrombin and other coagulation proteins are contained in the patients' plasma in different quantities. This influences the test result. A blood withdrawal involves the risk of local side effects, such as hematoma, or generalized side effects, such as inflammation of the vein or transmission of infection (e.g. hepatitis, HIV).

Thus, the problem underlying the present invention is to provide new means for an efficient detection of thrombin inhibitors which overcome the shortcomings of the protocols known in the art.

The solution to the above technical problem is achieved by the embodiments characterized in the claims.

In particular, the present invention relates to a method for detecting at least one direct thrombin inhibitor in a sample, comprising the steps of:
(a) providing a sample containing at least one direct thrombin inhibitor;
(b) providing a composition containing thrombin;
(c) providing a composition containing a chromogenic substrate conjugated to a detectable substance;
(d) mixing the sample of step (a) with the composition of step (b) and the composition of step (c) under conditions which allow the binding of the at least one direct thrombin inhibitor to thrombin and which allow the thrombin to release the detectable substance from the chromogenic substrate;
(e) measuring the amount of released detectable substance, wherein the sample does not contain citrated blood plasma.

According to the present invention, the term "thrombin" does not underlie a specific restriction and may include any activated thrombin obtained from a natural source or via recombinant DNA technology, or a biologically active derivative thereof.

As used herein, the term "biologically active derivative" includes any derivative of a protein, protein complex or polypeptide having substantially the same functional and/or biological properties of thrombin such as binding properties, and/or the same structural basis, such as a peptidic backbone. The polypeptide sequences of the functionally active derivatives may contain deletions, additions and/or substitution of amino acids whose absence, presence and/or substitution, respectively, do not have any substantial negative impact on the activity of the polypeptide, e.g. amino acids which are located in a part of the polypeptide sequence that does not contribute to the biological activity of the protein. Minor deletions, additions and/or substitutions of amino acids of the respective polypeptide sequences which are not altering the biological activity of said polypeptide are also included in the present application as biologically active derivatives.

A thrombin obtained from a natural source may be any thrombin isolated from a blood product derived from a mammal. In a preferred embodiment of the present application, the mammal is selected from the group consisting of mouse, human, rat, cat, dog, and monkey. In a particularly preferred embodiment, the thrombin is isolated from a blood product of a human. In a preferred embodiment of the present application, the thrombin is isolated from a blood product selected from the group consisting of whole blood, serum, or plasma, including isolated blood compounds and processed blood products. A thrombin obtained from a natural source may be a thrombin obtained by isolating from a blood product as defined above and subsequently activating the isolated thrombin, e.g. by using any thromboplastin or by using viper venom, such as Russell's viper venom.

The thrombin according to the present invention may be produced by any method known in the art. This may include any method known in the art for the production of recombinant DNA by genetic engineering, e.g. via reverse transcription of RNA and/or amplification of DNA. This includes methods which comprise the recombinant production of thrombin and the subsequent activation of prothrombin, e.g. by using thromboplastin of by using Russell's viper venom, in order to obtain thrombin.

For example, the recombinant DNA coding for prothrombin, e.g. a plasmid, may also contain a DNA sequence encoding a selectable marker for selecting the cells which have been successfully transfected with the plasmid. In an example of the present invention, the plasmid may also confer resistance to a selectable marker, e.g. to the antibiotic drug G418, by delivering a resistance gene, e.g. the neo resistance gene conferring resistance to G418.

The production of thrombin may include any method known in the art for the introduction of recombinant DNA into eukaryotic cells by transfection, e.g. via electroporation or microinjection. For example, the recombinant expression of human thrombin can be achieved by introducing an expression plasmid containing the human prothrombin encoding DNA sequence under the control of one or more regulating sequences such as a strong promoter, into a suitable host cell line by an appropriate transfection method resulting in cells having the introduced sequences stably integrated into the genome. The calcium-phosphate coprecipitation method is an example of a transfection method which may be used according to the present invention.

The production of thrombin may also include any method known in the art for the cultivation of said transformed cells, e.g. in a continuous or batchwise manner, and the expression of the thrombin, e.g. constitutive or upon induction. In one specific example of the present invention the nucleic acid coding for thrombin contained in the host organism of the present invention is expressed via an expression mode selected from the group consisting of induced, transient, and permanent expression. Any expression system known in the art or commercially available can be employed for the expression of a recombinant nucleic acid encoding thrombin, including the use of regulatory systems such as suitable, e.g. controllable, promoters, enhancers etc.

The production of thrombin may also include any method known in the art for the isolation of the protein, e.g. from the culture medium or by harvesting the transformed cells. For example, the thrombin-producing cells can be identified by isolating single-cell derived populations i.e. cell clones, via dilution after transfection and optionally via addition of a selective drug to the medium. After isolation the identified cell clones may be cultivated until confluency in order to enable the measurement of the thrombin content of the cell culture supernatant by enzyme-linked immuno-sorbent assay (ELISA) technique.

Additionally, the production of thrombin may include any method known in the art for the purification of thrombin, e.g. via anion exchange chromatography or affinity chromatography. In one preferred embodiment thrombin can be purified from cell culture supernatants by semi-affinity calcium-dependent anion exchange chromatography, e.g. in an endotoxin-free system. The purified thrombin or thrombin may be analyzed by methods known in the art for analyzing recombinant proteins, e.g. the ELISA technique. In addition, the protein integrity and activity may be assessed. It is within the knowledge of a person skilled in the art to choose the optimal parameters, such as buffer system, temperature and pH for the respective detection system to be used.

In one specific example of the present invention, the thrombin according to the present invention is expressed in a host cell type with the ability to perform posttranslational modifications. The ability to perform posttranslational modifications of thrombin or thrombin expressing host cell lines may be for example analyzed by mass-spectrometric analysis.

The host cell type used for the recombinant production of thrombin may be any mammalian cell, preferably with the ability to perform posttranslational modifications of thrombin. There is no particular limitation to the media, reagents and conditions used for culturing the cells in the cell culture used for the recombinant production of thrombin including culturing the cells in a continuous or batchwise manner. The desired thrombin protein which has been expressed by the cells of the and which, dependent on the transfection/vector-system used, is contained in the cells or secreted into the medium for culturing cells, can be isolated/recovered from the cell culture using methods known in the art, as mentioned herein before.

The term "thrombin" as used herein comprises any thrombin which is obtained by producing and isolating thrombin according to any method available in the prior art and disclosed herein followed by a subsequent activation of prothrombin, e.g. by using thromboplastin or Russell's viper venom.

The term "at least one direct thrombin inhibitor" as used herein relates to any naturally occurring or artificially synthesized inhibitor of thrombin activity. In a preferred embodiment of the present invention, the thrombin inhibitor is selected from the group, consisting at present of dabigatran, ximelagatran, argatroban, hirudins, modified hirudins and/or others in development. In a more preferred embodiment of the present invention, the thrombin inhibitor is dabigatran.

The sample containing at least one direct thrombin inhibitor provided in step (a) of the method for detecting at least one direct thrombin inhibitor in a sample according to the present invention, may be any sample which contains at least one direct thrombin inhibitor, and which does not contain citrated blood plasma. In one embodiment of the present invention, the sample may be derived from a naturally occurring system, preferably a sample containing a body fluid or components derived from a body fluid. In one embodiment of the present invention, the sample may be a naturally occurring system such as a solution selected from the group consisting of serum, saliva, urine, bile, lymph, tissue, like e.g. bladder or kidney, cerebrospinal fluid and/or other body fluids. In a preferred embodiment of the present invention, the sample comprises urine.

In a particularly preferred embodiment of the present invention, the sample comprises urine and the at least one direct thrombin inhibitor is dabigatran.

Further, the sample may comprise a solution derived from naturally occurring systems, e.g. a solution containing isolated body fluid compounds or processed body fluids. In another embodiment of the present invention, the sample may comprise cells or tissue samples obtained from a mammal. Methods for obtaining the above samples are known in the prior art.

The sample may be derived from a mammal, preferably a mammal selected from the group consisting of human, mouse, rat, pig, cat, dog, horse, goat, cattle, cow, and monkey and/or others. In a preferred embodiment of the present invention, the sample is derived from a human. In another embodiment of the present invention, the sample contains isolated body fluid compounds or processed body fluids derived from a mammal, preferably a mammal selected from the group consisting of human, mouse, rat, pig, cat, dog, horse, goat, cattle, cow, and monkey and/or others. In a preferred embodiment of the present invention, the sample contains isolated body fluid compounds or processed body fluids derived from a human.

In a more preferred embodiment of the present invention, the sample is derived from a patient to which the thrombin has been administered before step (a) of the method for detecting at least one direct thrombin inhibitor in a sample according to the present invention. The patient can be selected from the group consisting human, mouse, rat, pig, cat, dog, horse, goat, cattle, cow, and monkey and/or others. Most preferably, the patient is a human being. In a preferred embodiment of the present invention, the sample is a sample as defined herein.

In a preferred embodiment, the sample is pre-purified before step (a) of the method for detecting at least one direct thrombin inhibitor in a sample according to the present invention. In a more preferred embodiment of the present invention, the pre-purification comprises the step of removing impurities that prevent the thrombin inhibitor from binding to thrombin.

The composition containing at least one thrombin provided in step (b) of the method for detecting at least one direct thrombin inhibitor in a sample according to the present invention may be any composition containing at least one thrombin and may also contain suitable buffer salts. In a preferred embodiment of the present invention the composition containing at least one thrombin is isotonic within the physiological limits of the pH value and may be of normal or low ionic strength.

According to the present invention the chromogenic substrate conjugated to a detectable substance provided in step (c) of the method for detecting at least one direct thrombin inhibitor in a sample according to the present invention is covalently linked to at least one detectable substance. The term "detectable substance" does not exhibit any particular limitation and may be selected from the group consisting of radioactive labels, fluorescent dyes, compounds having an enzymatic activity, magnetic labels, antigens, and compounds having a high binding affinity for a detectable substance. A compound having an enzymatic reactivity such as the enzyme luciferase which produces a light signal upon contact with the respective substrate can also be used as a detectable substance which may be linked covalently to said substrate. Coupling a detectable substance to an antigen allows the detection of the substance by an antibody/enzyme-complex (the enzyme being e.g. phosphatase) catalysing a detectable color reaction when using a suitable substrate. A compound with a high binding affinity for a different detectable substance such as biotin which binds to a detectable substance covalently linked to e.g. streptavidin, is a further possibility for making a substance detectable. In a preferred embodiment of the present application, the detectable substance is para-nitroaniline.

The chromogenic substrate conjugated to a detectable substance provided in step (c) of the method for detecting at least one direct thrombin inhibitor in a sample according to the present invention is any chromogenic substrate conjugated to a detectable substance which can be cleaved by thrombin so that the detectable substance is released from the chromogenic substrate. In a preferred embodiment of the present invention, the conjugation of the chromogenic substrate to the detectable substance is via the linker Isoleucine-Glutamine-Glycine-Arginine-X (Ile-Glu-Gly-Arg-X) or via the linker Glycine-Proline-Arginine-X (Ile-Pro-Arg-X), wherein X is any positively charged amino acid. In a preferred embodiment of the present application, the chromogenic substrate conjugated to a detectable substance is an amino acid sequence which contains the sequence Ile-Glu-Gly-Arg-X or Ile-Pro-Arg-X, wherein X is any amino acid except of proline, at the site where the detectable substance binds, provided that the structure of the chromogenic substrate conjugated to a detectable substance is such that thrombin cleaves the sequence Ile-Glu-Gly-Arg-X or Ile-Pro-Arg-X under physiological conditions at room temperature.

In a preferred embodiment of the present invention, the chromogenic substrate conjugated to a detectable substance is a fluorogenic substance. In a more preferred embodiment of the present invention, the chromogenic substrate conjugated to a detectable substance is selected from the group consisting of Benzyl-Isoleucine-Glutamine-Glycine-Arginine-para-nitroaniline hydrochloride, Tosyl-Glycine-Proline-Arginine-para-nitroaniline, rhodamine 110, and bis-p-tosyl-L-glycyl-L-prolyl-L-arginine amide. In a particularly preferred embodiment of the present invention the chromogenic substrate conjugated to a detectable substance is Benzyl-Isoleucine-Glutamine-Glycine-Arginine-para-nitroaniline hydrochloride.

The conditions suitable for the binding of the at least one direct thrombin inhibitor to thrombin and which allow the thrombin to release the detectable substance from the chromogenic substrate in step (d) of the method for detecting at least one direct thrombin inhibitor in a sample according to the present invention may take place in a buffer solution. If a buffer solution is used in step (d) of the method for detecting at least one direct thrombin inhibitor in a sample according to the present invention, it may contain any compound which does not negatively affect inhibitor-thrombin-complex forming and the release the detectable substance from the chromogenic substrate by thrombin. In a preferred embodiment of the method for detecting at least one direct thrombin inhibitor in a sample according to the present invention, the conditions in step (d) comprise the use of a the buffer solution which is isotonic and within the physiological limits of the pH value. It may be of normal or low ionic strength. The buffer salts used in step (d) of the method for detecting at least one direct thrombin inhibitor in a sample according to the present invention may be any buffer salt as long as said buffer salt does not negatively affect the inhibitor-thrombin-complex forming and the release the detectable substance from the chromogenic substrate by thrombin.

Step (d) of the method for detecting at least one direct thrombin inhibitor in a sample according to the present invention may be carried out under any conditions suitable for binding of the at least one direct thrombin inhibitor to thrombin and which allow the thrombin to release the detectable substance from the chromogenic substrate without any limitation. This comprises e.g. any suitable temperature, time period and agitation of the buffer solution. In a preferred embodiment of the present invention, the incubation is carried out at a temperature ranging from about 20° C. to about 37° C. for from about 1 to about 30 minutes. In a more preferred embodiment of the present invention, the incubation is carried out at about 37° C. for about 20 minutes.

In a preferred embodiment, the method for detecting at least one direct thrombin inhibitor in a sample according to the present invention includes the step of removing the chromogenic substrate after step (d) and before step (e). The chromogenic substrate can be removed by methods well known in the art. Examples for the removal of the chromogenic substrate are, but not limited to, for example the use of antibodies or enzymes specifically binding the chromogenic substrate. In a preferred embodiment of the present application, the antibodies or enzymes, preferably coagulation enzymes, specifically binding the chromogenic substrate are bound to a support as defined herein. Further, the chromogenic substrate may be covalently linked to a compound with a high binding affinity for a different compound such as biotin which binds to a compound covalently linked to e.g. streptavidin, or to a magnetic compound is a further possibility for removing the chromogenic substrate.

The removal of the chromogenic substrate can be carried out by standard methods. For example, if the one or more or all of the antibodies or enzymes, preferably coagulation enzymes, specifically binding the chromogenic substrate is conjugated to biotin, the chromogenic substrate can be removed by binding the biotin to streptavidin and the subsequent removal of the biotin-streptavidin-complex, e.g. by centrifugation or, if the streptavidin is conjugated to a suitable support, like a resin material, by column chromatography. As an alternative, if the antibodies or enzymes, preferably coagulation enzymes, specifically binding the chromogenic substrate are covalently linked to a magnetic compound, the chromogenic substrate can be removed by binding said chromogenic substrate via a magnetic compound having the opposite polarity. The reaction conditions to perform the removal of the chromogenic substrate depend upon the removal method selected. It is within the knowledge of the person skilled in the art to choose the optimal parameters, such as buffer system, temperature and pH for the respective removal system to be used.

The reaction conditions for measuring the amount of released detectable substance in step (e) of the method for detecting at least one direct thrombin inhibitor in a sample according to the present invention depend upon the detection method selected. It is within the knowledge of the person skilled in the art to choose the optimal parameters, such as buffer system, temperature and pH for the respective detection system to be used.

The measuring step (e) of the above-defined method may comprise one or more detection method(s) selected from the group consisting of immunoblotting, immunoprecipitation, immunocapture, monoclonal antibody immobilization of platelet antigens or enzyme linked immuno sorbent assay (ELISA), flow cytometry, protein array technology, spectroscopy, mass spectrometry, chromatography, surface plasmonic resonance, fluorescence extinction and/or fluorescence energy transfer. The detection method for measuring the detectable substance can, for example, be selected from the group consisting of an enzyme assay, a chromogenic assay, a lumino assay, a fluorogenic assay, and a radioimmune assay. The reaction conditions to perform detection of the detectable label depend upon the detection method selected. It is within the knowledge of the person skilled in the art to choose the optimal parameters, such as buffer system, temperature and pH for the respective detection system to be used. In a preferred embodiment of the present application, the detectable substance para-nitroaniline and the released para-nitroaniline is detected via measuring the absorption of the sample at 405 nm.

If the detectable substance is detected via antibodies specifically binding the detectable substance, the antibodies may be immobilized on a support, preferably a solid support. The term "support" does not have any specific limitations, and relates, for example, to an insoluble polymer material, which can be an organic polymer, such as polyamide or a vinyl polymer (e.g. poly(meth)acrylate, polystyrene and polyvinyl alcohol, or derivatives thereof), a natural polymer such as cellulose, dextrane, agarose, chitin and polyamino acids, or an inorganic polymer, such as glass or metallohydroxide. The support can be in the form of a microcarrier, particles, membranes, strips, paper, film, pearls or plates, such as microtiter plates or microarrays. The term "microarray" as used herein may mean any arrangement of the antibodies in addressable locations on a support resulting in a so-called "biochip". The support may also be used as resin material, which can be used in a column chromatography.

In a preferred embodiment of the present invention, the method for detecting at least one direct thrombin inhibitor in a sample according to the present invention is a method for point-of-care testing using a sample which is not plasma or whole blood. When the method for detecting at least one direct thrombin inhibitor in a sample according to the present invention is a method for point-of-care testing, the composition containing thrombin provided in step (b) of the method for detecting at least one direct thrombin inhibitor in a sample according to the present invention and/or the composition containing a chromogenic substrate conjugated to a detectable substance provided in step (c) of the method for detecting at least one direct thrombin inhibitor in a sample according to the present invention are immobilized on a test strip. The mixing of the sample of step (a) with the composition of step (b) and/or the composition of step (c) in step (d) is obtained by applying a test sample as defined herein on the respective position on the test strip, on which the composition containing thrombin and/or the composition containing composition containing a chromogenic substrate conjugated to a detectable substance is immobilized. The measuring of the amount of released substance according to step (e) of the method for detecting at least one direct thrombin inhibitor in a sample according to the present invention is accomplished by inserting the test strip into an instrument being suitable for measuring of the amount of released substance. In a preferred embodiment of the present invention, the instrument is a transportable, portable or handheld instrument.

In a preferred embodiment of the present invention, the method for detecting at least one direct thrombin inhibitor in a sample according to the present invention is a method for point-of-care testing and the composition containing thrombin provided in step (b) of the method for detecting at least one direct thrombin inhibitor in a sample according to the present invention is immobilized on a test strip and the composition containing a chromogenic substrate conjugated to a detectable substance provided in step (c) of the method for detecting at least one direct thrombin inhibitor in a sample according to the present invention is not immobilized on the test strip. The mixing of the sample of step (a) with the composition of step (b) in step (d) is obtained by applying a test sample as defined herein on the respective position on the test strip, on which the composition containing thrombin is immobilized.

In one embodiment, the test strip is inserted into an instrument being suitable for providing the composition of step (c) and for measuring of the amount of released substance. The mixing of the sample of step (a) and the composition of step (b) with the composition of step (c) in step (d) is obtained by applying the composition of step (c) on the respective position on the test strip, on which the composition containing thrombin is immobilized and already mixed with the test sample, in the test instrument. The measuring of the amount of released substance according to step (e) of the method for detecting at least one direct thrombin inhibitor in a sample according to the present invention is accomplished by the instrument into which the test strip has been inserted. In a preferred embodiment of the present invention, the instrument is a transportable, portable or handheld instrument.

In another embodiment, the composition of step (c) is applied manually, for example by using a pipette. The mixing of the sample of step (a) and the composition of step (b) with the composition of step (c) in step (d) is obtained by applying the composition of step (c) on the respective position on the test strip, on which the composition containing thrombin is immobilized and already mixed with the test sample. The measuring of the amount of released substance according to step (e) of the method for detecting at least one direct thrombin inhibitor in a sample according to the present invention is accomplished by assessing optical changes of the mixed sample, for example a change of color. This assessment can be carried out, for example by comparing the optical appearance of the mixture with the optical appearance of a negative control and/or a positive control, which can be for example provided on the test strip or in a manual provided by the manufacturer of the test strip. The optical changes of the mixed sample can also be carried out, for example by comparing the optical appearance of the mixture with the optical appearance of positive controls having different concentrations of the direct thrombin inhibitor, for example obtained using a standard dilution series.

In another preferred embodiment of the present invention, the method for detecting at least one direct thrombin inhibitor in a sample according to the present invention is a method for point-of-care testing and the composition containing a chromogenic substrate conjugated to a detectable substance provided in step (c) of the method for detecting at least one direct thrombin inhibitor in a sample according to the present invention is immobilized on a test strip and the composition containing thrombin provided in step (b) of the method for detecting at least one direct thrombin inhibitor in a sample according to the present invention is not immobilized on the test strip. The mixing of the sample of step (a) with the composition of step (c) in step (d) is obtained by applying a test sample as defined herein on the respective position on the test strip, on which the composition containing a chromogenic substrate conjugated to a detectable substance is immobilized.

In one embodiment, the test strip is inserted into an instrument being suitable for providing the composition of step (b) and for measuring of the amount of released substance. The mixing of the sample of step (a) and the composition of step (c) with the composition of step (b) in step (d) is obtained by applying the composition of step (b) on the respective position on the test strip, on which the composition containing a chromogenic substrate conjugated to a detectable substance is immobilized and already mixed with the test sample, in the test instrument. The measuring of the amount of released substance according to step (e) of the method for detecting at least one direct thrombin inhibitor in a sample according to the present invention is accomplished by the instrument into which the test strip has been inserted. In a preferred embodiment of the present invention, the instrument is a transportable, portable or handheld instrument.

In another embodiment, the composition of step (b) is applied manually, for example by using a pipette. The mixing of the sample of step (a) and the composition of step (b) with the composition of step (c) in step (d) is obtained by applying the composition of step (b) on the respective position on the test strip, on which the composition containing a chromogenic substrate conjugated to a detectable substance is immobilized and already mixed with the test sample. The measuring of the amount of released substance according to step (e) of the method for detecting at least one direct thrombin inhibitor in a sample according to the present invention is accomplished by assessing optical changes of the mixed sample, for example a change of color. This assessment can be carried out, for example by comparing the optical appearance of the mixture with the optical appearance of a negative control and/or a positive control, which can be for example provided on the test strip or in a manual provided by the manufacturer of the test strip. The optical changes of the mixed sample can also be carried out, for example by comparing the optical appearance of the mixture with the optical appearance of positive controls having different concentrations of the direct thrombin inhibitor, for example obtained using a standard dilution series.

When the method for detecting at least one direct thrombin inhibitor in a sample according to the present invention is a method for point-of-care testing, the direct thrombin inhibitor, the sample, the composition containing thrombin, the thrombin, the composition containing a chromogenic substrate conjugated to a detectable substance, the chromogenic substance, the detectable substance, and/or each of steps (a) to (e) are preferably as defined herein. In a particularly preferred embodiment of the present invention, the chromogenic substrate conjugated to a detectable substance provided in step (c) is selected from the group consisting of radioactive labels, compounds having an enzymatic activity, magnetic labels, antigens, and compounds having a high binding affinity for a detectable substance.

In a preferred embodiment of the present invention, the method for detecting at least one direct thrombin inhibitor in a sample according to the present invention is a method for point-of-care testing as defined herein, the sample is urine and the direct thrombin inhibitor is dabigatran. Preferably, (i) the composition containing thrombin provided in step (b) or (ii) the composition containing a chromogenic substrate conjugated to a detectable substance provided in step (c) are immobilized on a test strip. In a preferred embodiment, the chromogenic substrate conjugated to a detectable substance is Benzyl-Isoleucine-Glutamine-Glycine-Arginine-para-nitroaniline hydrochloride. The test strip is inserted into the urine sample. Then, (i) in case the composition containing thrombin provided in step (b) is already immobilized on the test strip, the composition containing a chromogenic substrate conjugated to a detectable substance provided in step (c) is added, or (ii) in case the composition containing a chromogenic substrate conjugated to a detectable substance provided in step (c) is already immobilized on the test strip, the composition containing thrombin provided in step (b) is added. The more optical changes of the mixed sample can be observed, preferably the more yellow the mixed sample turns, the less thrombin inhibitors are in the sample.

In a preferred embodiment of the present invention, the method for detecting at least one direct thrombin inhibitor in a sample according to the present invention is a method for point-of-care testing as defined herein, and the sample is serum or urine. In this embodiment, the composition comprising thrombin provided in step (b) of the method of the present invention, and the composition containing a chromogenic substrate conjugated to a detectable substance provided in step (c) of the method of the present invention are immobilized on a test strip. In particular, a first matrix, e.g. a polyvinylchloride (PVC) matrix, is used as material to attach other matrices, e.g. compressed glucose or filter paper. One of these other matrices is incubated with the above composition comprising thrombin, and the other is incubated with the above composition containing a chromogenic substrate conjugated to a detectable substance. These other matrices are attached to the first matrix at different locations, preferably on two sides of the first matrix, thus forming the test strip. For performing the method of the present invention, the test strip is incubated with the sample for a short time, e.g. one or two seconds. After that, the test strip is incubated in a medium, e.g. a buffer, preferably Tris-buffer. Upon incubation, the matrices release thrombin, the chromogenic substrate conjugated to a detectable substance, and the sample into the medium. Subsequently, the thrombin reacts with the substrate and, if present, the direct thrombin inhibitor in the sample. After a certain reaction time, e.g. 10 minutes, a colored compound is formed, indicating the reaction between the thrombin and the substrate. The color formed in the absence of inhibitor may be yellow, e.g. when a substrate releasing paranitroanilin is used. In case high concentrations of inhibitor are present in the sample, no color develops. The amount of color formed correlates to the concentration of inhibitor in the sample. In a preferred embodiment, another color can be added to one of the above other matrices, e.g. methylene blue which changes into green upon the development of the yellow color. Accordingly, the above medium is green in case no inhibitor is present in the sample, and blue in case of high concentrations of inhibitor in the sample. Any other additional color for producing a different color than yellow may be used as well.

The antibodies specifically binding the detectable substance or the antibodies specifically binding the chromogenic substrate, if the chromogenic substrate is removed, can be immobilized on the support directly by covalent coupling or via a carrier such as a linker molecule or an antibody immobilized on the support. Further, the antibodies specifically binding the detectable substance or the support may be covalently linked to a detectable label which may be any suitable detectable label known in the art. In a preferred embodiment of the present invention, the detectable label is biotin or a magnetic substance.

In a preferred embodiment of the present invention, the method for detecting at least one direct thrombin inhibitor in a sample according to the present invention further contains after step (e) a step
(f) determining the amount of thrombin inhibitor in the sample by correlating the amount of released detectable substance with the amount of thrombin inhibitor in the sample.

The amount of released detectable substance decreases with an increase of thrombin inhibitor in the sample.

The quantification of the detectable substance, preferably resulting in the determination of the amount of thrombin inhibitor in the sample, can be carried out by standard methods. In a preferred embodiment of the present invention, the amount of thrombin inhibitor in the sample is calculated from a calibration curve obtained by a thrombin inhibitor in defined amounts.

The present invention further relates to a use of a composition containing thrombin for monitoring the course of treatment with at least one direct thrombin inhibitor in a patient. In another preferred embodiment the use of a composition containing thrombin for monitoring the course of treatment with at least one direct thrombin inhibitor in a patient comprises the method for detecting at least one direct thrombin inhibitor in a sample according to the present invention as defined herein. In a preferred embodiment of the present invention, the thrombin, the thrombin inhibitor, and/or the patient is as defined herein. In a preferred embodiment of the present invention, the course of treatment is monitored by detecting at least one direct thrombin inhibitor in a sample, more preferably in a test sample comprising serum, urine, or any other body fluid.

The present invention further relates to a composition containing thrombin for use in monitoring the course of treatment with direct thrombin inhibitors in a patient for diagnostic purposes. In a preferred embodiment, the present invention relates to a composition containing thrombin for use in monitoring the course of treatment with direct thrombin inhibitors in a patient for diagnostic purposes, wherein an elevated risk for thrombosis is associated with an increase of thrombin inhibitors in the sample. In a preferred embodiment of the present invention, the thrombin, the thrombin inhibitor, and/or the patient is as defined herein.

A further embodiment of the present invention relates to a diagnostic kit for monitoring the course of treatment with direct thrombin inhibitors in a patient comprising a composition containing thrombin and composition containing a chromogenic substrate conjugated to a detectable substance. In a preferred embodiment of the present invention, the kit contains further any means for carrying out the method for detecting at least one direct thrombin inhibitor in a sample according to the present invention as defined herein. In particular, the kit may contain one or more of the following: a chromogenic substrate conjugated to a detectable substance as defined herein, antibodies specifically binding the detectable substance as defined herein, thrombin and modified thrombin proteins specifically binding the chromogenic substrate as defined herein, a support with immobilized antibodies or thrombin enzymes specifically binding the detectable substance as defined herein, a support with immobilized antibodies specifically binding the chromogenic substrate as defined herein, buffer solutions as defined herein, reaction containers, and/or means for measuring the amount of released detectable substance as defined herein, including buffers, when appropriate. In a preferred embodiment of the present invention, the thrombin, the direct thrombin inhibitor, and/or the patient is as defined herein.

It one of the aspects underlying the present invention to measure the concentration/activity of a direct thrombin inhibitor like dabigatran with a chromogenic test from samples for measuring other blood components (liver parameters, kidney parameters, cholesterol, etc.) or blood count without an additional blood withdrawal for the blood coagulation. Using the present invention the concentration of a thrombin inhibitor like dabigatran in urine without a further blood withdrawal can be determined. Instead of dabigatran, other direct inhibitors of thrombin in matrices other than plasma can be measured with a chromogenic test.

Direct thrombin inhibitors inhibit exogenous thrombin also without the presence of antithrombin or endogenous thrombin. Thus, the measurement from serum, urine, and other matrices becomes possible. The invention solves the problem that the direct thrombin inhibitors inhibit the colorant para-nitroaniline from a chromogenic substrate in a dose-dependent manner only in the presence of exogenous thrombin. A separate blood withdrawal for the coagulation measurement is not necessary any more using the method according to the present invention. For an examination in urine, a blood withdrawal can be omitted. The risk of side effects of a blood withdrawal is reduced (serum tube, blood count tube) or eliminated (urine).

It is essential for the present invention that dabigatran and other direct thrombin inhibitors inhibit exogenously added thrombin without the presence of other coagulation proteins.

Thereby, the concentration/activity of thrombin inhibitors, like dabigatran, in serum and other biological matrices can be detected.

The advantages of the invention are that using the method according to the present invention, the side effects and risks associated with a blood withdrawal are reduced (detection in serum) or eliminated (detection in urine), and the special taking of a "coagulation tube" is not necessary.

The basis for the present invention is the fact that for a photometric determination of the inhibition of thrombin no fibrinogen, and for the direct inhibitors of thrombin no antithrombin are necessary as cofactors. It is essential for the present invention that the concentration/activity of medicaments that directly inhibit thrombin can be quantified via the inhibition of exogenous thrombin in and on media/matrices by means of a thrombin specific chromogenic substrate, which are not plasma (FIG. 1).

The figures show:

FIG. 1: Overview of the reactants in the test system and the reaction process and the measurement in a preferred embodiment of the present invention.

Figure 2:
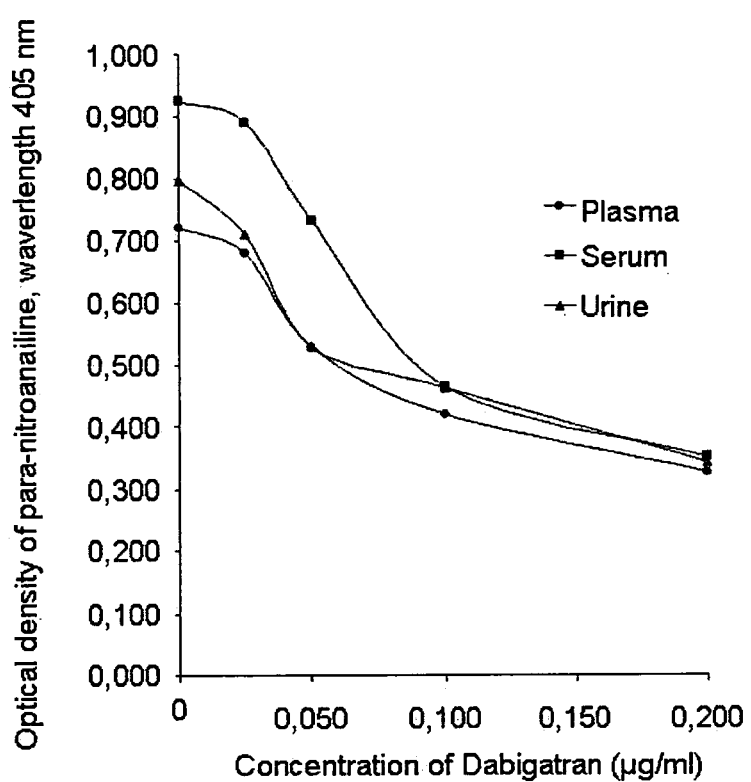

FIG. 2: Illustration of the inhibition of thrombin by increasing quantity of dabigatran (x axis) in plasma (method so far), in serum and urine (new methods). Small quantities of dabigatran inhibit little/no thrombin, so that much colorant is released from the chromogenic substrate (high absorption, y axis, nm=nanometer of the wavelength for measuring the colorant). The less dabigatran is needed to inhibit the release of the colorant (low values of the absorption), the more sensitive the detection for dabigatran becomes. The influencing factors present in plasma are not present in serum and urine.

Figure 3:
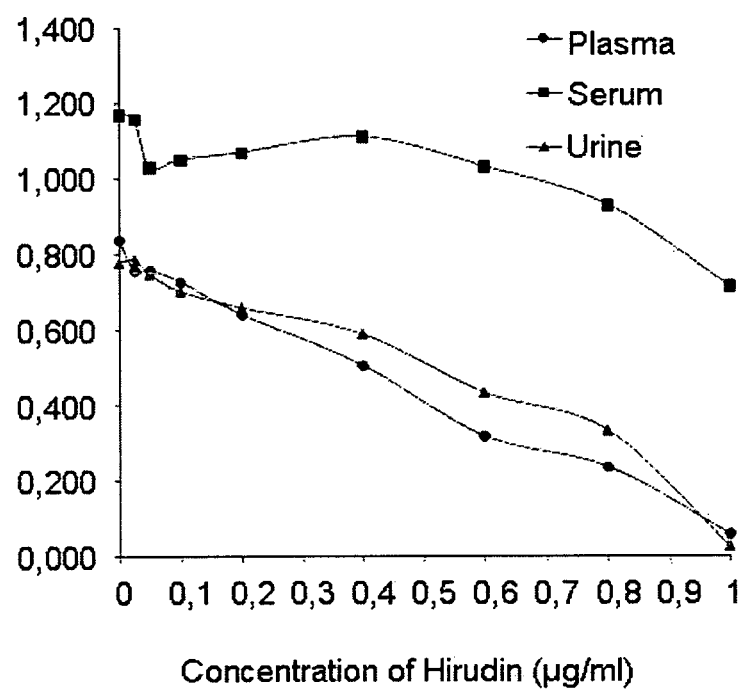

FIG. 3: Illustration of the inhibition of thrombin by increasing quantity of hirudin (x axis) in plasma (method so far), in serum and urine (new methods). See explanation for FIG. 2.

The present invention will now be further illustrated in the following examples without being limited thereto.

EXAMPLES

Example 1 a) Measurement of Dabigatran in Serum with Thrombin and S2238
Reagents: Solution 1: Aqua Destillata
Solution 2:

| Tris-Buffer | Tris | 6.06 g |
|---|---|---|
| | NaCl | 10.23 g |
| | EDTA | 2.79 g |
| | pH | 8.4 |
| | ad 1000 ml Aqua destillata | |

Solution 3:
serial dilution Dabigatran with 0 ng/ml, 50 ng/ml, 100 ng/ml, 150 ng/ml, 300 ng/ml, 500 ng/ml, 700 ng/ml, dissolved in serum
Solution 4:
Thrombin 71 nkat (Chromogenix, Essen Germany) dissolved in 10 ml A. dest.
Solution 5:
Chromogenic substrate S-2238™ 25 mg (Chromogenix, Essen Germany)
dissolved in 33.7 ml A. dest
Solution 6:
acidic acid: 50%
a.1) Test Description: Standard Curve for the Determination of Dabigatran in Serum

| 25 μl serum with known concentration of Dabigatran, 1:15 diluted in tris buffer + |
|---|
| 25 μl Thrombin |
| 2 min. incubation at 37° C. + |
| 50 μl Chromogenic substrate S-2238 ™ |
| 20 min. incubation at 37° C. + |
| 25 μl acetic acid 50% |
| Measurement at 405 nm |
| Preparation of a standard curve (OD versus ng/ml) |

Test Description: Determination of Serum Samples

| 25 μl serum, containing Dabigatran, 1:15 diluted in tris buffer + |
|---|
| 25 μl Thrombin |
| 2 min. incubation at 37° C. + |
| 50 μl Chromogenic substrate S-2238 ™ |
| 20 min. incubation at 37° C. + |
| 25 μl acidic acid 50% |
| Measurement at 405 nm |

Calculation of the concentration of Dabigatran was carried out using the standard curve. The concentration of Dabigatran was determined by the optical density (OD) of the sample.

b) Measurement of Dabigatran in Urine with Thrombin and Chromogenic Substrate S-2238™
Reagents are the same as in the measurement of Dabigatran in urine.

Test Description: Standard Curve

```
25 μl Dabigatran in urine +
25 μl Thrombin
2 min. incubation at 37° C. +
50 μl Chromogenic substrate S-2238 ™
20 min. incubation at 37° C. +
25 μl acidic acid 50%
Measurement at 405 nm
Preparation of a standard curve (OD versus ng/ml)
```

Test Description: Determination of Urine Samples

```
25 μl urine +
25 μl Thrombin
2 min. incubation at 37° C. +
50 μl Chromogenic substrate S-2238 ™
20 min. incubation at 37° C. +
25 μl acidic acid 50%
Measurement at 405 nm
``` c) Factor IIa Inhibition of Dabigatran (in Serum)
Reagents:
Dabigatran
  Chromogenic substrate S-2238™ (25 mg) (Chromogenix) are dissolved in 40 ml aqua. dest.
  Thrombin (SIGMA T-8885): per vail 10 U
  aprotinin is diluted to 500 KIU/ml with aqua. dest.

| Tris-Buffer: | Tris | 6.06 g |
| | NaCl | 10.23 g |
| | EDTA | 2.79 g |
| | pH 8.4 is adjusted with 1.0M HCl |
| | ad 1000 ml aqua. dest. |

Thrombin/Aprotinin-Working Solution:
  Dissolve 1 ampule thrombin 10 U with 1 ml aqua. dest and is brought to 11.5 ml with Tris-Buffer. Additionally, add 1 ml aprotinin 500 KIU/ml.
Prepare Standard Curve:
  Dilute dabigatran in the concentrations: 10, 8, 6, 4, 2, 1, 0.5, 0.25 μg/ml in Tris-Buffer.
  Subsequently dilute each standard point again with serum 1:10.
  Final concentrations. 1, 0.8, 0.6, 0.4, 0.2, 0.1, 0.05, 0.025 μg/ml
Accomplishment of Test:

| Standard or sample | 10 μl |
| Tris-Buffer | 100 μl |
| Incubation 5 minutes | |
| Thrombin-working solution | 100 μl |
| Incubation 60 sec | |
| Chromogenic substrate | 50 μl |
| Incubation 5 min. | |
| Acidic acid | 50 μl |
| Measurement at 405 nm | |

Each serum sample needs its own blank value, i.e.

```
50 μl acidic acid +
50 μl chromogenic substrate +
100 μl thrombin-working solution +
100 μl Tris-Buffer +
10 μl sample to be tested
``` d) Factor IIa Inhibition of Dabigatran (in Urine)
Reagents:
Dabigatran
  Chromogenic substrate S2238™ (25 mg) (Chromogenix) are dissolved in 40 ml aqua. dest.
  Thrombin (SIGMA T-8885): per vail 10 U
  aprotinin is diluted to 500 KIU/ml with aqua. dest.

| Tris-Buffer: | Tris | 6.06 g |
| | NaCl | 10.23 g |
| | EDTA | 2.79 g |
| | pH 8.4 is adjusted with 1.0M HCl |
| | ad 1000 ml aqua. dest. |

Thrombin/Aprotinin-Working Solution:
  Dissolve 1 ampule thrombin 10 U with 1 ml Aqua. dest and is brought to 11.5 ml with Tris-Buffer. Additionally, add 1 ml aprotinin 500 KIU/ml.
Prepare Standard Curve:
  Dilute dabigatran in the concentrations: 10, 8, 6, 4, 2, 1, 0.5, 0.25 μg/ml in Tris-Buffer.
  Subsequently dilute each standard point again with urine 1:10.
  Final concentrations: 1, 0.8, 0.6, 0.4, 0.2, 0.1, 0.05, 0.025 μg/ml
Accomplishment of Test:

| Standard or sample | 10 μl |
| Tris-Buffer | 100 μl |
| Incubation 5 minutes | |
| Thrombin-working solution | 100 μl |
| Incubation 60 sec | |
| Chromogenic substrate | 50 μl |
| Incubation 5 min. | |
| Acidic acid | 50 μl |
| Measurement at 405 nm | |

Each urine sample needs its own blank value, i.e.

```
50 μl acidic acid +
50 μl chromogenic substrate +
100 μl thrombin-working solution +
100 μl Tris-Buffer +
10 μl sample to be tested
``` d) Factor IIa Inhibition of Dabigatran (in Urine)
Reagents:
Dabigatran
  Chromogenic substrate S-2238™ (25 mg) (Chromogenix) are dissolved in 40 ml aqua. dest.
  Thrombin (SIGMA T-8885): per vail 10 U
  aprotinin is diluted to 500 KIU/ml with aqua. dest.

| Tris-Buffer: | Tris | 6.06 g |
| | NaCl | 10.23 g |
| | EDTA | 2.79 g |
| | pH 8.4 is adjusted with 1.0M HCl |
| | ad 1000 ml aqua. dest. |

Thrombin/Aprotinin-Working Solution:
  Dissolve 1 ampule thrombin 10 U with 1 ml Aqua. dest and is brought to 11.5 ml with Tris-Buffer. Additionally, add 1 ml aprotinin 500 KIU/ml.
Prepare Standard Curve:
  Dilute dabigatran in the concentrations: 10, 8, 6, 4, 2, 1, 0.5, 0.25 μg/ml in Tris-Buffer.

Subsequently dilute each standard point again with urine 1:10.

Final concentrations: 1, 0.8, 0.6, 0.4, 0.2, 0.1, 0.05, 0.025 µg/ml

Accomplishment of Test:

| Standard or sample | 10 µl |
|---|---|
| Tris-Buffer | 100 µl |
| Incubation 5 minutes | |
| Thrombin-working solution | 100 µl |
| Incubation 60 sec | |
| Chromogenic substrate | 50 µl |
| Incubation 5 min. | |
| Acidic acid | 50 µl |
| Measurement at 405 nm | |

Each urine sample needs its own blank value, i.e.

| 50 µl acidic acid + |
|---|
| 50 µl chromogenic substrate + |
| 100 µl thrombin-working solution + |
| 100 µl Tris-Buffer + |
| 10 µl sample to be tested | e) Factor IIa Inhibition of Hirudin (in Urine)

Reagents:

Hirudin

Chromogenic substrate S-2238™ (25 mg) (Chromogenix) are dissolved in 40 ml aqua. dest.

Thrombin (SIGMA T-8885): per vail 10 U aprotinin is diluted to 500 KIU/ml with aqua. dest

| Tris Buffer: | Tris | 6.06 g |
|---|---|---|
| | NaCl | 10.23 g |
| | EDTA | 2.79 g |
| | pH 8.4 is adjusted with 1.0M HCl | |
| | ad 1000 ml aqua. dest. | |

Thrombin/Aprotinin-Working Solution:

Dissolve 1 ampule thrombin 10 U with 1 ml Aqua. dest and is brought to 11.5 ml with Tris-Buffer. Additionally, add 1 ml aprotinin 500 KIU/ml.

Prepare Standard Curve:

Dilute hirudin in the concentrations: 10, 8, 6, 4, 2, 1, 0.5, 0.25 µg/ml in Tris-Buffer.

Subsequently dilute each standard point again with urine 1:10.

Final concentrations: 1, 0.8, 0.6, 0.4, 0.2, 0.1, 0.05, 0.025 µg/ml

Accomplishment of Test:

| Standard or sample | 10 µl |
|---|---|
| Tris-Buffer | 100 µl |
| Incubation 5 minutes | |
| Thrombin-working solution | 100 µl |
| Incubation 60 sec | |
| Chromogenic substrate | 50 µl |
| Incubation 5 min. | |
| Acidic acid | 50 µl |
| Measurement at 405 nm | |

Each urine sample needs its own blank value, i.e.

| 50 µl acidic acid + |
|---|
| 50 µl chromogenic substrate + |
| 100 µl thrombin-working solution + |
| 100 µl Tris-Buffer + |
| 10 µl sample to be tested | f) Calculation of the Concentration of Dabigatran and Hirudin

The concentration of Dabigatran and Hirudin was carried out using the standard curve. The concentration of Dabigatran/Hirudin was determined by the optical density (OD) of the sample.

The direct thrombin inhibitor dabigatran was added to samples of plasma, serum, and urine in different concentrations. The reagent thrombin (from Chromogenix) and chromogenic substrate (S2238 from Chromogenix) were added to the samples, incubated and measured in a photometer at a wavelength of 405 nanometers (nm). Dabigatran/Hirudin inhibits the activity of thrombin and thus the release of para-nitroaniline from the chromogenic substrate S2238 in a dose-dependent manner (FIGS. 2 and 3).

Due to missing antithrombin and other cofactors for heparins and missing thrombin and other coagulation proteins in the assay run, the detection of dabigatran and other thrombin inhibitors is less sensitive and susceptible to influences (FIGS. 2 and 3).

Our studies have shown that dabigatran in serum and urine can be measured with a chromogenic test without the addition of plasma.

g) Determination of Dabigatran on Strips

Strips are coated at the tip with adsorbing material (Merck AG, Darmstadt). This area is incubated with 10 microliter of Thrombin solution or with S2238 solution each, respectively. Urine (10 mikoliter) was incubated on the strips for 15 min at room temperature with human urine from a patient treated with dabigatran. The strips are overlied so that the reactants can penetrate between the areas of the strips. If the urine contains dabigatran the area with the reagents remains pail (white). Decreasing the amount of dabigatran the color changes to yellow. The color can be quantified using the Color Colorpicker 1.0 program. This program quantifies the colors red, yellow and blue. The corresponding values for the color blue are given in relation to the concentration of dabigatran in urine. The urine of the patient was diluted 1:10 and 1:100 by a urine sample not containing dabigatran to obtain low concentrations of dabigatran. Mean values were calculated from double values. The values were calculated from a curve obtained from urine of a healthy person spiked with dabigatran (Table 1).

TABLE 1

Colorimetry of the strips containing small areas prepared with the reagents for determination of dabigatran in urine.

| Value of the Colorpicker | concentration of dabigatran |
|---|---|
| 47.5 | 85 ng |
| 41.5 | 8.5 ng |
| 34.5 | 0.85 ng |

The above is a demonstration of the prove of concept for the point of care analysis of dabigatran in human urine. The appearing color depends on the concentration of dabigatran in urine. The results have to be read as follows: high concentration of dabigatran inhibits the release of para-nitroaniline by thrombin resulting in no/white/clear color.

Low concentrations of dabigatran result in a release of para-nitroaniline and a yellow color.

The invention claimed is:

1. A method for detecting dabigatran in an untreated urine sample, comprising the steps of:
   (a) providing a urine sample containing dabigatran;
   (b) providing a composition containing thrombin;
   (c) providing a composition containing a chromogenic substrate conjugated to a detectable substance;
   (d) mixing the urine sample of step (a) with the composition of step (b) and the composition of step (c) under conditions which result in the binding of dabigatran to thrombin and release the detectable substance from the chromogenic substrate;
   (e) measuring the amount of released detectable substance;
   wherein the urine sample does not contain citrated blood plasma, and
   wherein the chromogenic substrate conjugated to a detectable substance is selected from the group consisting of Tosyl-Glycine-Proline-Arginine-para-nitroaniline, and rhodamine 110, bis-p-tosyl-L-glycyl-L-prolyl-L-arginine amide.

2. The method according to claim 1, which is a point-of-care testing.

3. The method according to claim 2, wherein the composition containing thrombin provided in step (b) or the composition containing a chromogenic substrate conjugated to a detectable substance provided in step (c) are immobilized on a test strip.

4. A method for monitoring the course of treatment with dabigatran in a patient, wherein the method comprises the method according to claim 1.

5. A method for monitoring the course of treatment with dabigatran in a patient for diagnostic purposes, wherein the method comprises the method according to claim 1.

6. The method of claim 5, wherein an elevated risk for thrombosis is associated with an increase of dabigatran in the sample.

7. The method of claim 1, wherein the amount of released detectable substance decreases with an increase of dabigatran in the urine.

8. The method of claim 1, where the urine sample is a human urine sample from a patient treated with dabigatran.

* * * * *